United States Patent [19]

Rigutto

[11] 4,279,594

[45] Jul. 21, 1981

[54] DENTAL HAND MIRROR

[75] Inventor: Martin A. Rigutto, Roseburg, Oreg.

[73] Assignee: Reflek Products, Incorporated, Roseburg, Oreg.

[21] Appl. No.: 85,879

[22] Filed: Oct. 18, 1979

[51] Int. Cl.³ .............................................. A61C 1/00
[52] U.S. Cl. ......................................... 433/31; 433/95
[58] Field of Search .................................... 433/31, 30

[56] References Cited

U.S. PATENT DOCUMENTS

| | | | |
|---|---|---|---|
| 1,905,633 | 4/1933 | Feltham | 433/30 |
| 1,925,981 | 9/1933 | Hopkins | 433/31 |
| 2,711,586 | 6/1955 | Groves | 433/95 |
| 2,809,430 | 10/1957 | Darber | 433/30 |
| 2,834,109 | 5/1958 | O'Hara | 433/30 |
| 3,052,031 | 9/1962 | Piscitelli | 433/30 |
| 3,082,762 | 3/1963 | Gnehn | 433/30 |
| 3,164,904 | 1/1965 | Barnes | 433/30 |
| 3,250,005 | 5/1966 | White | 433/30 |
| 3,638,013 | 1/1972 | Keller | 433/31 |
| 3,849,889 | 11/1974 | Rosander | 433/30 |
| 3,969,824 | 7/1976 | Wden et al. | 433/30 |
| 3,986,266 | 10/1976 | Vellender | 433/30 |

*Primary Examiner*—Robert Peshock
*Attorney, Agent, or Firm*—Klarquist, Sparkman, Campbell, Leigh, Whinston & Dellett

[57] ABSTRACT

A dental hand mirror unit includes a generally hollow handle portion which supports a mirror at one end and has its other end releasably coupled to a cap or valve member. Air is fed through the cap member and handle portion and is directed outwardly along the upper surface of the mirror to prevent it from fogging. Rotation of the cap member controls the flow of air to the mirror as desired. In one embodiment, light from a light dispersion element positioned in a chamber beneath a two-way mirror passes outwardly through the mirror and into a patient's mouth. In addition, light is transmitted to such dispersion element by a bundle of optic fibers positioned within an optical fiber passageway portion of the dental hand mirror unit.

13 Claims, 16 Drawing Figures

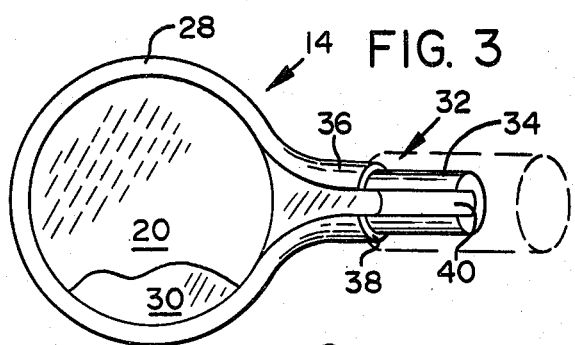
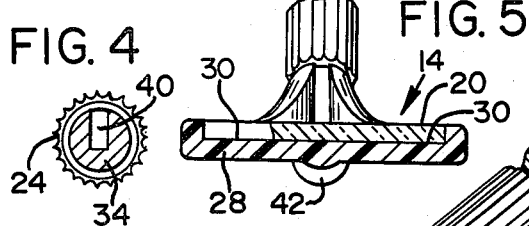
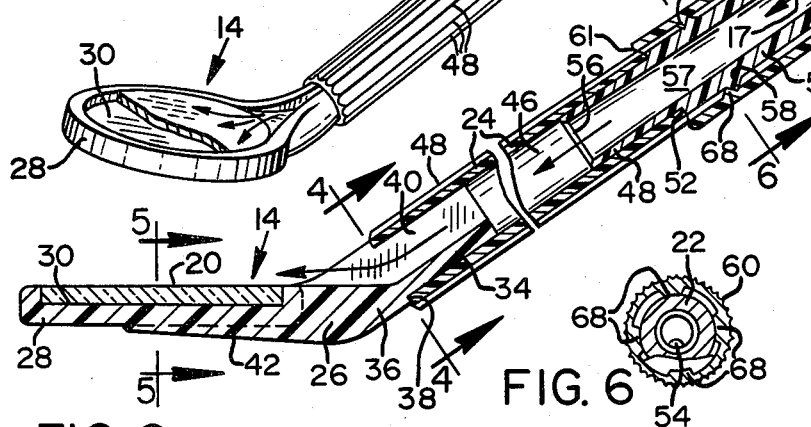
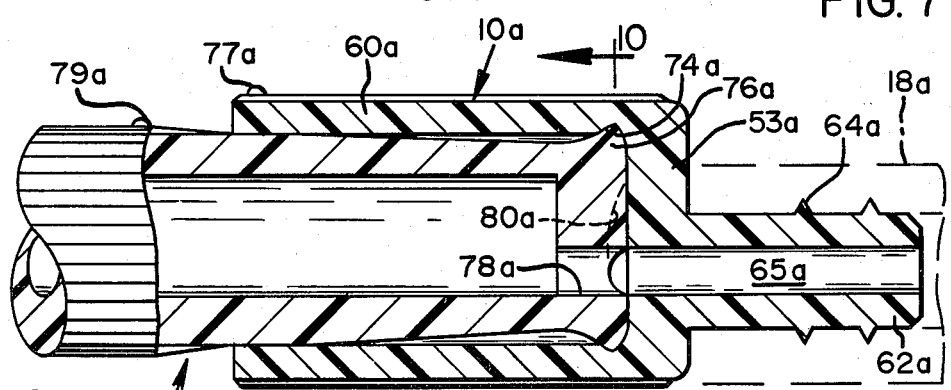
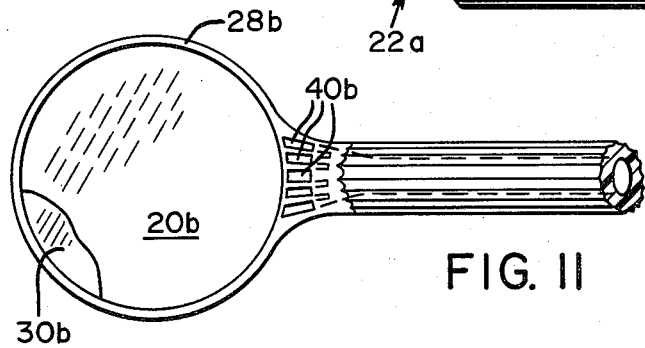
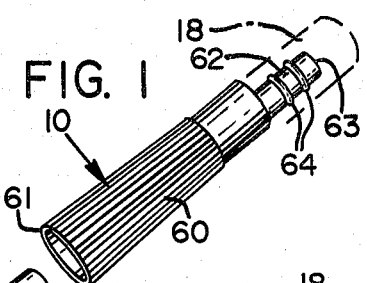
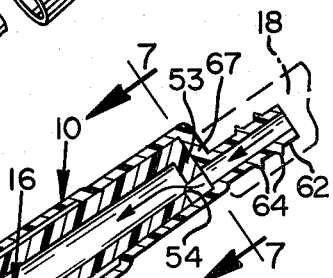

DENTAL HAND MIRROR

BACKGROUND OF THE INVENTION

1. Field of the Invention

The present invention relates to a dental hand mirror unit having an air stream directed towards the surface of a mirror portion of the unit for cleaning purposes and also to such a hand mirror unit having an illuminating light source.

2. Description of the Prior Art

During use, the reflective surface of a dental hand mirror unit commonly used by dentists quickly becomes obstructed and blurred by, among other things, spray from high-speed drills, dental material and tooth debris, fog and mist. As a result, the quality and workmanship by a dentist can be impaired.

It has therefore been customary for dentists to frequently remove such mirrors from a patient's mouth to clean the reflective surface and then reposition them. This is a tedious, time-consuming and costly process. In addition, interruptions to clean a mirror not only interrupt a dentist's concentration, but also detract from the high degree of accuracy required during a wide variety of dental procedures.

Numerous attempts have been made to solve the problem of foggy, unclean dental mirrors. One typical prior art approach is to direct a stream of air to the surface of a mirror either through a hollow handle of the mirror unit or through an air supply tube clipped to the handle. U.S. Pat. Nos. 1,905,633; 2,809,430; 2,834,109; and 3,082,762 are exemplary of such attempts. However, such devices suffer from many common drawbacks. For example, they lack mechanisms for conveniently controlling the volume of air supplied to the surface of the mirror. That is, many of these devices simply supply a constant volume of air regardless of the needs of the specific dental procedure being performed. Others provide some degree of control of the stream of air through complex and costly mechanisms positioned at a location separated from the hand mirror unit, such as at a console in the dental office. However, such devices are difficult to operate because a dentist must stop work on a patient to adjust the air supplied to the mirror.

Various dental hand mirror units have also been proposed with cumbersome mechanisms on the handle of the unit for controlling the volume of air supplied to the surface of the mirror. As disclosed in U.S. Pat. Nos. 1,925,981, 3,052,031, and 3,164,904, such devices typically include a spring biased push-button operated valve projecting from the handle of the mirror unit. Depressing the button permits a stream of air to flow through the handle of the mirror unit and onto the mirror surface. However, controls of this nature hamper the work of a dentist. For example, the projecting push-buttons may catch on the lip or gum tissue of a patient, and cause much discomfort. In addition, debris and saliva from a patient apparently may bypass the push-buttons and enter the interior of the handle of such mirrors, making such devices extremely difficult to sterilize. Also, mirrors of this type are relatively costly to manufacture and are subject to breakdown as the biasing springs wear.

Still other types of devices have been suggested which control the flow of both water and air, either simultaneously or alternately across the surface of a hand mirror. Examples of such hand mirror units are disclosed in U.S. Pat. Nos. 3,969,924 and 3,986,266. Devices of this type are inherently more complex and costly because both air and water are supplied to the mirror.

In addition, applicant is not aware of any dental hand mirror units which provide an illuminating light source either separate from or together with an air supply for cleaning the surface of the mirror.

Therefore, until the present invention, there has not been a practical, workable, self-cleaning dental hand mirror unit available to dentists, nor such a device capable of illuminating an area within a patient's mouth in which a dentist is working.

SUMMARY OF THE INVENTION

It is an object of the invention to provide an improved dental hand mirror unit having an air supply for cleaning the surface of a mirror portion of the unit.

It is a further object of the invention to provide a compact, light-weight, dental hand mirror unit of the type including an air supply for cleaning the surface of a mirror portion of the unit.

It is still another object of the invention to provide a dental hand mirror unit having an easily adjustable air control mechanism included within the handle of the unit for controlling the volume of air supplied to the surface of a mirror portion of the unit.

It is another object of the invention to provide a dental hand mirror unit which is relatively inexpensive such that it may be disposed after use, thereby eliminating hygiene problems associated with sterilizing dental hand mirrors.

It is another object of the invention to provide an improved dental hand mirror unit which illuminates a patient's mouth during use.

These and other objects, features and advantages of the invention will become apparent from the following description which references the accompanying drawings.

BRIEF DESCRIPTION OF THE DRAWINGS

FIG. 1 is a perspective view of a dental hand mirror unit partially in section, in accordance with the invention;

FIG. 2 is a longitudinal-sectional view of the dental hand mirror unit of FIG. 1;

FIG. 3 is a partially broken-away top plan view of a mirror assembly portion of the dental hand mirror unit of FIG. 1;

FIG. 4 is a cross-sectional view of a dental hand mirror unit in accordance with the invention taken along lines 4—4 of FIG. 2;

FIG. 5 is a partially sectional view of the mirror assembly portion of a dental hand mirror unit in accordance with the invention taken along lines 5—5 of FIG. 2;

FIG. 6 is a cross-sectional view of a dental hand mirror unit in accordance with the invention taken along lines 6—6 of FIG. 2;

FIG. 7 is a cross-sectional view of a dental hand mirror unit in accordance with the invention taken along lines 7—7 of FIG. 2;

FIG. 8 is a top plan view of one form of an air flow restriction disc for insertion into a cap section of a dental hand mirror unit of FIG. 1;

FIG. 9 is a longitudinal-sectional view of another embodiment of a cap section of a dental hand mirror unit in accordance with the invention;

FIG. 10 is a cross-sectional view of the cap section of FIG. 9 taken along lines 10—10 thereof;

FIG. 11 is a partially broken-away top plan view of another form of mirror assembly in accordance with the invention;

DETAILED DESCRIPTION OF PREFERRED EMBODIMENTS

Figure 13:
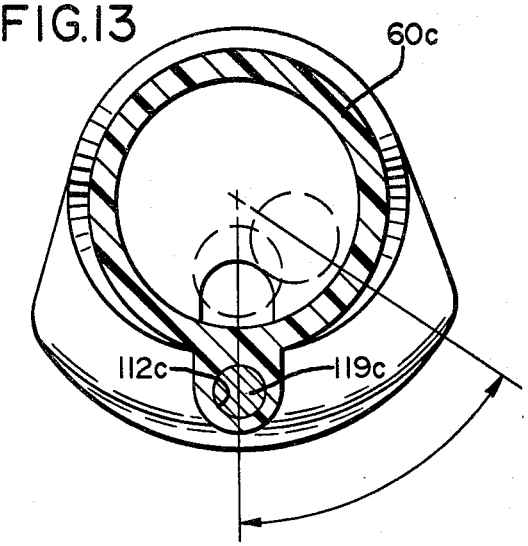
FIG. 13 is a cross-sectional view of the dental hand mirror unit of FIG. 12 taken generally along lines 13—13.

With reference to FIG. 1, one embodiment of a dental hand mirror unit in accordance with the invention includes a cap section 10, handle section 12 and mirror section 14. When assembled, as shown in FIG. 2, these sections define an interior air passageway which is indicated generally at 16. Air from an air supply hose 18 coupled to cap section 10 may pass, as indicated by arrows 17, through passageway 16 and along the exposed upper surface of a mirror 20 forming a part of mirror section 14. As a result, the exposed surface of mirror 20 is cleaned of fog, mist, and other debris. Air is supplied to hose 18 in a conventional manner from an air source commonly found in a dentist's office for operating dental equipment.

The handle and mirror sections 12, 14 may be an integral unit and formed of any suitable material, such as stainless steel with mirror 20 being formed of glass with its rear surface coated with an appropriate reflective material. However, preferably, the handle and mirror sections 12, 14 are of multipiece construction. Thus, handle section 22 includes a coupling portion 22 and a body portion 24 while mirror section 14 comprises a single piece mirror supporting portion 26. When handle and mirror sections 12, 14 are assembled, mirror support portion 26 is connected to one end portion of body 24 while the other end portion of body 24 is connected to coupling portion 22. Cap section 10, coupling portion 22, body portion 24, and mirror support portion 26 are preferably formed of a semi-rigid curable polymer material such as polyvinyl chloride. Portions 22, 24 and 26 may be interconnected in any suitable manner, such as by press fitting or solvent welding them together. As a result, the dental hand mirror unit is lightweight and relatively low cost so that the assembled handle section 12 and mirror section 14, the portion of the dental hand mirror which contacts a patient's mouth, is disposable after use. Therefore problems associated with sterilization of dental hand mirrors are minimized. Furthermore, with this multi-section construction, the dental hand mirror of the invention is easily manufactured as its components may be molded or extruded without difficulty. Also, the device is compact having, in one embodiment, an overll length, including cap section 10, of approximately six and one-half inches.

With reference to FIGS. 1 through 5, mirror support portion 26 includes a platelike mirror mounting portion 28 having a generally planar recessed upper surface 30 to which the rear surface of mirror 20 is mounted, as by epoxy. Mirror support portion 26 also includes a longitudinally elongated stem section 32 projecting upwardly from mirror mounting portion 28. Preferably, a thirty to forty-five degree angle is provided between a generally horizontal plane containing the upper surface of mirror 20 and the longitudinal axis of stem 32, which corresponds to the longitudinal axis of handle section 12. These angles facilitate the use of the mirror within the patient's mouth. More specifically, in the preferred embodiment, this angle is established at thirty-four degrees. Stem 32 includes a first or upper stem portion 34 of a reduced outside dimension in comparison to a second or lower stem portion 36. Thus, a shoulder 38 is defined at the transition between the respective upper and lower stem sections 34, 36.

A slot 40 is provided in an upper region of stem portion 32 and forms a portion of air passageway 16. Slot 40 has a generally U-shaped cross-section as it passes through upper stem portion 34. Also, slot 40 becomes both wider and shallower progressing through the lower stem portion 36 toward mirror 20. As a result, air travelling through slot 40 is dispersed along substantially the entire exposed surface of mirror 20. A reinforcing rib 42 extends from stem portion 36 beneath mirror supporting portion 28 and rigidifies mirror section 14.

Body portion 24 preferably comprises a hollow tubular member which is open at its ends and defines an interior passageway 46 having a circular cross-section of a constant diameter. Passageway 46 forms a portion of air passageway 16. Plural elongated ridges 48 on the exterior surface of body portion 24 are provided to facilitate gripping of the dental hand mirror unit. When assembled, upper stem portion 34 is inserted into one end of body portion 24 with shoulder 38 abutting the end surface of this main body portion.

Coupling portion 22 comprises a hollow frustoconical member with a first end section 48 having an outside diameter which is reduced relative to the outside diameter of the adjoining midsection 50 of the coupling portion. Thus, an annular shoulder 52 is defined at the transition between end section 48 and midsection 52. Furthermore, first end section 48 is sized to fit snugly within the passageway 46 of body portion 24 with shoulder 52 abutting the upper end surface of body portion 24 when the dental hand mirror is assembled. The second end of coupling portion 22, opposite the first end, is capped by a closure portion 52 which in turn is pierced by an air supply aperture 54. Also, the first end is open at 56 so that an air passageway 57 is defined between aperture 54 and opening 56. Passageway 57 forms an additional section of air passageway 16.

In addition, for reasons explained below, an annular coupling ring 58 projects outwardly from the exterior surface of the mid-section 50 of the coupling portion 22.

Cap section 10 comprises a frustoconical hollow body 60 with a coupling end 61 for engaging coupling portion 22 and a hollow cylindrical tube engaging portion 62 projecting outwardly from an end cap 67 at its opposite end 63. Annular spaced rings 64 projecting from the outer surface of cylinder 62 grip the interior surface of tube 18 to retain tube 18 in place and provide an airtight seal between the tube and cap section. Thus, a passageway 65 is provided through cylinder portion 62 which also is a part of air passageway 16. In addition, plural fastening ridges project inwardly from the inner surface of cap body 60 adjacent to its coupling end 61. As shown in FIG. 6, four such ridges 68 spaced about the interior perimeter of cap body 60 are included in the illustrated embodiment, each of which is in a common plane. Thus, when cap section 10 is mounted on handle section 12, with the interior face of an end cap 67 abutting the exterior face of cap closing section 53, ridge sections 68 snap over ring 58 and releasably secure cap section 10 in place. Also, the interior dimension of cap body 60 is reduced adjacent closing section 53 to fit tightly against the exterior surface of coupling portion 22 when the mirror unit is assembled to thereby provide a substantially airtight connection between cap section 10 and handle section 12. Also, the abutting relationship of the adjacent faces of closing section 53 to end cap 67 contributes to this seal.

Therefore, with this construction, a dentist need merely snap a mirror assembly including a handle portion 12 and mirror section 14 into a cap section 10 and the device is ready for use. Furthermore, following use on one patient, the assembled mirror and handle sections may be easily removed from cap section 10 and discarded.

More importantly, ridges 68 and ring 58 comprise one means of rotatably coupling cap section 10 to handle section 12 such that the cap section is free to rotate or pivot about its longitudinal axis. With reference to FIG. 7, the cap section may be rotated either clockwise or counterclockwise to place the passageway 65 through cylinder 62 in any desired degree of alignment with aperture 54. For example, in FIG. 7 aperture 54 is shown in alignment with passageway 65 to permit a maximum volume of air to flow through air passageway 16 and to the exposed surface of mirror 20. Typically, the maximum permissible air pressure within passageway 16 is established in the range of from four to fifteen pounds per-square-inch. Conversely, pivoting of cap section 10 in either direction causes a misalignment of passageway 65 with aperture 54 thereby reducing the air flow through the aperture in accordance with the degree of misalignment. Furthermore, the air flow is entirely shut off when aperture 54 is not in communication with passageway 65 as shown in dashed lines in FIG. 7. Thus, a dentist can conveniently and readily control the volume of air escaping over the mirror surface by merely twisting cap section 10 about its longitudinal axis as the dental hand mirror is used.

In certain applications, a small, thin, disc-like insert 70 may be positioned between the exterior face of cap closing member 53 and the interior face of end cap portion 67. Disc 70 defines a cut out or notched opening 72 which is sized smaller than aperture 54 so that, when the disc is inserted in place with notch 72 in alignment with aperture 54, the maximum air flow through the instrument is limited by the dimensions of notch 72 and not by the dimensions of aperture 54. Thus, by inserting such discs 70 with notches 72 of preselected sizes, a dentist may limit the maximum air flow permitted through the mirror unit as desired.

With reference to FIGS. 9 and 10, another form of cap section 10a and coupling portion 22a is illustrated. With this construction, the ring 58 and projecting ridges 68 are eliminated. Instead, the end of cap body 60a adjacent closing section 53a is of an enlarged interior diameter such that an annular recess 74a is defined in this region. Furthermore, coupling portion 22a is of frustoconical construction and has a flared end portion 76a which is disposed within recess 74a when the handle and cap sections are assembled. Thus, flared end portion 76a cooperates with the recess defining portion 74a of the cap section to releasably secure the assembly together while permitting rotation of the cap section about its longitudinal axis. An opening 78a of circular cross-section is defined through the flared end portion 76a and has a diameter which may be of varying size, but typically is of the same dimension as the diameter of passageway 65a through cylinder 62a. When the dental hand mirror unit of this embodiment is in its maximum air flow position, opening 78a is in alignment with passageway 65a. Indicia 77a on the exterior surface of cap section 10a is aligned with indicia 79a on the handle section when the mirror unit is in its maximum air flow position. Thus, by observing the relative positions of indicia 77a and indicia 79a, a dentist can quickly ascertain the volume of air supplied to the exposed mirror surface.

However, the exterior surface of flared end section 76a, as shown in FIG. 10, is recessed to define a chanel 80a which tapers from a section 81a sized to match the diameter of opening 78a to a section 82a of extremely narrow width. In addition, the depth of channel 80a progressively decreases moving from 81a to section 82a. As a result, when cap member 10a is rotated counterclockwise from its position shown in FIG. 9, the path between passageway 65a and opening 78a through channel 80a is progressively restricted. As a result, when the cap is turned in this direction the flow of air supplied to the exposed surface of the mirror is reduced. Furthermore, continued rotation in this direction eventually shuts off the air supply. In addition, clockwise rotation of the cap section from its position shown in FIG. 9, quickly shuts off the air supply as desired.

FIG. 11 discloses another form of mirror section in accordance with the invention in which plural, spaced apart, trapezoidal shaped openings 40b are provided for distributing the air from slot 40 across the upper surface of mirror 20b.

FIGS. 12 through 16 show a further form of dental hand mirror unit in accordance with the invention. In this embodiment, mirror 20c comprises a two-way mirror having a light source positioned beneath its exposed surface for emitting light through the mirror as indicated by arrows 100c and onto the region of a patient's mouth toward which the mirror is focused. Thus, in cooperation with the air supplied to clean the surface of the mirror, a dentist's vision of the work area is enhanced.

In the preferred embodiment of this form of dental hand mirror unit, light is transmitted to the mirror along a bundle of fiber optic fibers positioned in an optical passageway along the under side of the dental hand mirror. More specifically, mirror support portion 26c defines a hollow interior chamber 102c positioned beneath mirror 20c. In addition, support portion 26c defines a recessed shoulder 104c which supports the rear perimeter surface of the mirror. In addition, lower stem portion 36c defines an interior passageway 106c which communicates between chamber 102c and the shoulder 38c of mirror body portion 24c. In addition, body portion 24c defines a passageway 108c of cylindrical cross-section along its under side which communicates at one end, when mirror section 14c is assembled to body portion 24c, with passageway 106c. Passageway 108c is enlarged at its other end portion 110c for purposes explained below. Passageway 108c terminates adjacent to shoulder 52c of coupling portion 22c. Also, an additional passageway 112c, enlarged at its end 114c adjacent end portion 110c is provided along the underside of cap section 10c. Furthermore, a passageway 116c parallels tube 18c and communicates with the end of passageway 112c opposite end 114c.

Figure 14:
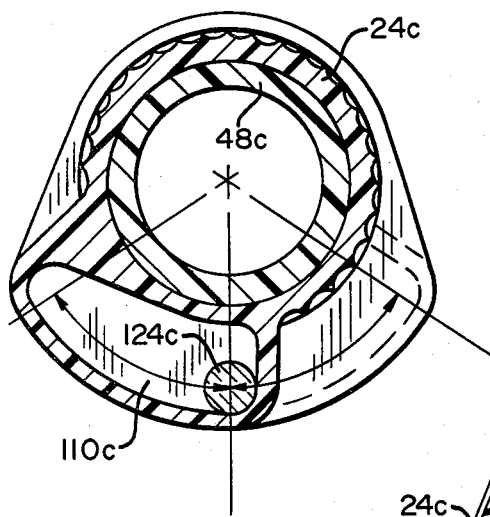
FIG. 14 is a cross-sectional view of the dental hand mirror unit of FIG. 12 taken along lines 14—14.
Figure 12:
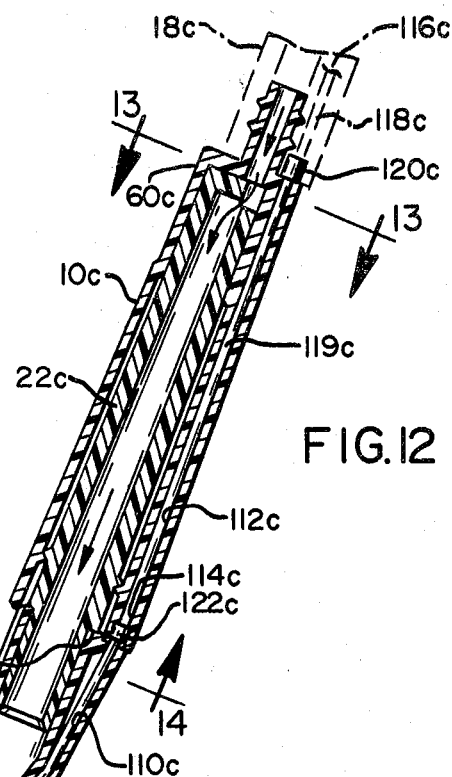
FIG. 12 is a longitudinal-sectional view of another form of dental hand mirror unit in accordance with the invention including a lighting mechanism for illuminating a patient's mouth.
Figure 15:
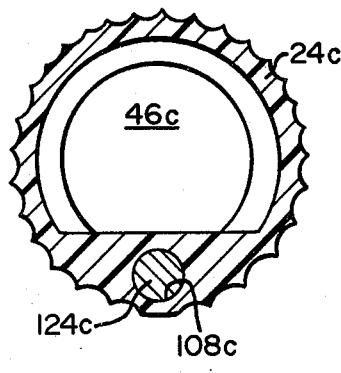
FIG. 15 is a cross-sectional view of a dental hand mirror unit of FIG. 12 taken along the lines of 15—15.
Figure 16:
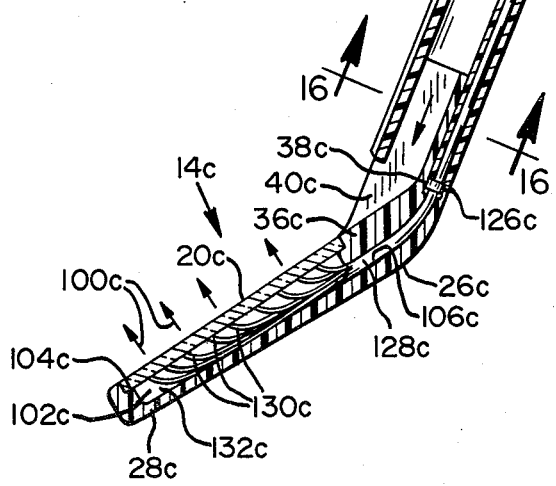
FIG. 16 is a cross-sectional view of a dental hand mirror unit of FIG. 12 taken along lines 16—16.

A bundle of fiberoptic fibers 118c positioned in passageway 116c transmits light from a remote light source, not shown, to a fiberoptic coupling 120c adjacent the end of tube 18c. A second fiberoptic bundle 119c extends within passageway 112c from coupling 120c to another fiberoptic coupling 122c adjacent passageway end portion 114c. A third fiber-optic bundle 124c extends from coupling 122c to another coupling 126c adjacent shoulder 38c at the mirror support member. Passageway 110c and 114c are enlarged at their junction to accommodate slack in the fiberoptic bundle which is taken up as cap section 10 is rotated, as illustrated in FIGS. 13 and 14, to control the volume of air supplied to the mirror.

Another fiberoptic bundle 128c extends from coupling 126c to chamber 102c. This latter bundle terminates in a light dispersion means behind mirror 20c. As one form of such light dispersion means, the bundle of fibers 128c is frayed with the individual fibers, some being shown at 130c, being bent gradually to extend in a direction generally normal to the lane of the mirror so that they direct light through the mirror to the area of the patient's mouth on which the mirror is focused. Fibers 130c are embedded in epoxy 132c to maintain them in place. Of course, alternate light dispersion means may be employed as desired. For example, reflecting surfaces such as mirrors disposed within chamber 102c may be positioned to direct light from fiber optic bundle 128 outwardly through mirror 20c. Also, the surfaces of mirror support section 126c which bound chamber 102c are preferably coated with reflective material to direct light within the chamber outwardly through mirror 20c.

While I have shown and described preferred embodiments of my invention, it will be apparent to those skilled in the art that changes and modifications may be made without departing from my invention in its broader aspects.

I claim:

1. A dental hand mirror unit comprising:
a generally hollow mirror assembly including a mirror end portion, coupling end portion and a handle portion interconnecting said mirror end portion and coupling end portion;
said mirror end portion including a mirror;
said mirror assembly defining a continuous uninterruptable airflow path from an inlet opening through said coupling end portion, through the interior of said mirror assembly and to an outlet at the mirror such that air entering said coupling end portion is distributed substantially over the mirror;
a cap section pivotally coupled to said coupling end portion for pivoting about the axis of said mirror assembly;
valve means responsive to the pivoting of said cap section about such axis for controlling the flow of air entering said coupling end portion and thereby the volume of air distributed over the mirror.

2. A dental hand mirror unit comprising:
a generally hollow mirror assembly including a mirror end portion and a coupling end portion;
said mirror end portion including a mirror;
said mirror assembly defining an airflow path from said coupling end portion through the interior of said mirror assembly and to the mirror such that air entering said coupling end portion is distributed substantially over the mirror;
a cap section pivotally and detactably coupled to said coupling end portion;
valve means responsive to the pivoting of said cap section for controlling the flow of air entering said coupling end portion and thereby the volume of air distributed over the mirror;
said coupling end portion being of generally circular cross section and including an end closure section which defines an air supply aperture which communicates between an exterior face of said closure section and the hollow interior of said mirror assembly, the air supply aperture being eccentrically positioned relative to the center of said end closure section;
said cap section being generally hollow and of generally circular cross section, said cap section having an end wall at a first end portion and defining an opening through a second end portion which is sized for receiving said coupling end portion therethrough for detachable coupling to said coupling end portion such that upon coupling of said cap section to said coupling end portion said cap section is concentric with said coupling end portion and such that the exterior face of said closure section is in abutting relationship with the interior face of said end wall, said end wall defining an air receiving opening for receiving air from an air supply and which is eccentrically positioned relative to the center of said end wall;
the air supply aperture and the air receiving opening being positioned such that pivoting said cap member moves the air receiving opening into and out of communicating alignment with the air supply aperture to thereby control the flow of air through the mirror assembly.

3. A dental hand mirror unit according to claim 2 including a generally circular disc for insertion between the opposing faces of said end wall and said closure section, said disc defining an eccentrically positioned notch or opening of a preselected size smaller than the size of the air supply aperture, said disc being inserted such that said notch is aligned with the air supply aperture, whereby the size of said notch limits the maximum air flow through the mirror assembly.

4. A dental hand mirror unit in accordance with claims 1 or 2 in which said cap section includes a visually observable exterior first indicia and said coupling section includes a visually observable exterior second indicia, such that the relative position of said first indicia to said second indicia provides an indication of the position of said cap section relative to said coupling portion and hence of the alignment of said air supply aperture and said air receiving opening, and thereby an indication of the air flow through the mirror assembly.

5. A dental hand mirror unit in accordance with claim 2 in which the exterior face of said closure section defines a tapered recess eccentrically position on said surface, a first end of such recess being sized to substantially the same dimension as said air supply aperture and the second end of such recess being substantially narrower in width, the depth of such recess progressively decreasing from said first to said second ends, said air receiving opening being positioned to communicating with said air supply aperture through said recess such that pivoting said cap section in one direction moves said air receiving opening away from said first end of the recess and toward said second end of the recess and thereby reduces the flow of air through the mirror assembly.

6. A dental hand mirror unit according to claim 2 in which said coupling end portion includes an annular ring projecting outwardly from its exterior surface, and in which said coupling section includes a coupling member projecting inwardly from its interior surface for snapping over and engaging said ring to prevent axial movement of said cap section relative to said coupling portion while permitting relative pivoting movement of said cap section and coupling portion.

7. A dental hand mirror unit according to claim 2 in which said coupling end portion is frusto-conical with a flared end portion adjacent said closure section, said cap section also being frusto-conical and defining an annular recess adjacent said end wall for receiving said flared end portion to prevent axial movement of said cap section relative to said coupling portion while permitting relative pivoting movement of said cap section and coupling portion.

8. A dental hand mirror unit according to claims 1 or 2 in which said mirror comprises a two-way mirror and said mirror end portion defines a hollow chamber beneath a major portion of said mirror, and also including light dispersion means disposed within said chamber for directing light outwardly from the chamber to the region of a patient's mouth on which the mirror is focused.

9. A dental hand mirror unit according to claim 8 in which said mirror assembly defines a first optical passageway communicating between said coupling end portion and said chamber and said cap section defines a second optical passageway communicating with said first optical passageway, and also including a bundle of fiberoptic fibers disposed within said first and second optical passageways for transmitting light therethough and to said light dispersion means.

10. A dental hand mirror assembly for connection to a cap section of a dental hand mirror unit comprising:
an elongated generally hollow body having a mirror end portion and a coupling end portion;
said mirror end portion including a mirror;
said body defining an air flow path from said coupling end portion through the interior of said body and to the mirror such that air entering said coupling end portion is distributed substantially over the mirror;
said coupling end portion being generally frusto-conical;
said coupling end portions including coupling means for pivotally coupling the cap section to said coupling end portion.

11. A dental hand mirror assembly according to claim 10 in which said coupling means comprise an annular ring projecting outwardly from an exterior surface of said coupling end portion.

12. A dental hand mirror assembly according to claim 10 in which said coupling means comprises a flared end portion of said coupling end portion.

13. A dental hand mirror unit comprising:
a generally hollow mirror assembly including a mirror section and a handle section;
said mirror section including a mirror, a mirror support section for supporting said mirror, and a hollow stem portion open at a first end for receiving a supply of air and open at a second end adjacent said mirror for distributing received air over the mirror;
said handle section including a generally hollow tubular elongated body portion open at its respective ends and a generally hollow frusto-conical coupling portion, open at its first end and having a closure section at its second end through which an eccentric air supply aperture is defined, said body portion being sized for receiving into one of its open ends, the step portion of said mirror section and for receiving with its opposite open end the first end of said coupling portion, whereby an air flow passageway is defined from said air supply aperture through said mirror assembly and to the mirror;
a frusto-conical cap section open at a first end and having an end wall at its opposite end through which an eccentric air receiving opening is defined, said cap member including a hose coupling portion for connection to an air supply hose and for directing air through said air receiving opening, said cap section being sized for receiving said coupling portion with the exterior face of said closure section abutting the interior face of said end wall, said cap member being concentric with said coupling portion; means for rotatively coupling said cap section to said coupling portion, such that rotation of said cap section brings the air supply aperture into communicative alignment with the air receiving opening with the degree of alignment and hence the flow of air to the mirror depending upon the rotational position of the cap section relative to the coupling portion.

* * * * *

UNITED STATES PATENT AND TRADEMARK OFFICE
CERTIFICATE OF CORRECTION

PATENT NO. : 4,279,594

DATED : July 21, 1981

INVENTOR(S) : Rigutto, Martin A.

It is certified that error appears in the above—identified patent and that said Letters Patent are hereby corrected as shown below:

Column 7, line 30, change "lane" to --plane--;

Column 8, line 9, change "detactably" to --detachably--;

Signed and Sealed this

Sixth Day of October 1981

[SEAL]

Attest:

GERALD J. MOSSINGHOFF

Attesting Officer    Commissioner of Patents and Trademarks